United States Patent [19]
Klar

[11] Patent Number: 6,007,846
[45] Date of Patent: *Dec. 28, 1999

[54] SCENTED BODY GEL HAVING PARTICULATE MATTER IN THE FORM OF GLITTER WITH PREDETERMINED SHAPES

[75] Inventor: Cindi Klar, New York, N.Y.

[73] Assignee: Townley Jewelry, Inc., New York, N.Y.

[ * ] Notice: This patent is subject to a terminal disclaimer.

[21] Appl. No.: 08/857,932

[22] Filed: May 16, 1997

[51] Int. Cl.[6] ..................................................... A61K 9/50

[52] U.S. Cl. ......................... 424/501; 424/401; 424/489; 424/59; 514/944

[58] Field of Search .................................... 424/401, 489; 514/944

[56] References Cited

U.S. PATENT DOCUMENTS

| | | | |
|---|---|---|---|
| 3,951,679 | 4/1976 | Bernhard et al. | 106/291 |
| 4,710,371 | 12/1987 | Palinczar | 424/47 |
| 4,731,242 | 3/1988 | Palinczar | 424/59 |
| 4,828,826 | 5/1989 | Franz et al. | 424/63 |
| 4,837,005 | 6/1989 | Brode, II et al. | 424/47 |
| 5,496,861 | 3/1996 | Rouse, 3 et al. | 514/778 |

*Primary Examiner*—José G. Dees
*Assistant Examiner*—Michael A. Williamson
*Attorney, Agent, or Firm*—Ezra Sutton

[57] ABSTRACT

A body gel composition having glitter contained therein comprising a surface active agent system for moisturizing the skin being in the range of 3 percent to 12 percent by weight of the body gel composition; at least one pH adjuster being in the range of 0.5% to 2.0% by weight of the body gel composition; a preservative system for preserving the body gel composition against microbial contamination being in the range of 0.40% to 2.4% by weight of the body gel composition; at least one anti-oxidant and light stabilizer for preventing oxidation of the body gel composition being in the range of 0.02% to 0.3% by weight of the body gel composition; a diluent in the form of water in the range of 50.0% to 70.0% by weight of the body gel composition; and suspended particulate matter having a plurality of predetermined glitter shapes for cosmetic ornamention of the body being in the range of 10.0% to 20.0% by weight of the body gel composition.

10 Claims, 1 Drawing Sheet

SCENTED BODY GEL HAVING PARTICULATE MATTER IN THE FORM OF GLITTER WITH PREDETERMINED SHAPES

FIELD OF THE INVENTION

The invention relates to a novel scented body gel composition which, when applied to the human body, provides glitter, moisture conditioning and protection to the skin. More particularly, this invention relates to a scented body gel having aesthetic qualities of fragrance, flavor, color, and particulate matter in the form of glitter with predetermined shapes such as stars, sunbursts, triangles, and the like and which fulfills the guidelines for cosmetic ingredients established by the Food and Drug Administration, as listed in the Federal Register: Volume 43, Number 166.

BACKGROUND OF THE INVENTION

Body gel compositions are widely used by females for body (skin) conditioning in which the body gel imparts cosmetic qualities of softer, wrinkle-free, and moistened skin to the user. Users of body gels are desirous of improved body gels for further cosmetic enhancing and aesthetic imparting qualities that will heighten a female's appearance, beauty and sex appeal.

There remains a need for a scented body gel which enhances the cosmetic and aesthetic appearance qualities for females, such that the body gel product would include a moisturizer, a fragrance, a flavor, a color, and a shaped glitter or sparkling effect on the skin.

DESCRIPTION OF THE PRIOR ART

Cosmetic formulations having particulate matter in the form of glitter have been disclosed in the prior art. For example, U.S. Pat. Nos. 4,710,371 and 4,731,242 to Palinczar disclose waterproof sunscreen compositions having chemical ingredients that include monohydric alcohols, polymeric film-formers, an active sunscreen agent, an acrylic acid crosslinked polymer, alkaline neutralizing agents, hydroxyl donors, suspended particulate matter ("glitter"), water-insoluble emollients and water. The above chemicals are used to form several variations of waterproof sunscreen compositions. These prior art patents do not teach a body gel having the composition of the present invention.

U.S. Pat. No. 4,915,935 to Corbett et al discloses a process for applying reflective particles ("glitter") to hair in the form of a styling foam (mousse). The styling foam composition has chemical ingredients that include a foaming agent, water-soluble hair setting resins, a propellant component, suspended particulate matter ("glitter"), and water. The chemicals in the '935 patent are used to form several variations of a styling mousse. This prior art patent does not teach a body gel having the composition of the present invention.

None of the prior art patents teach or disclose the ingredient composition of a body gel of the present invention that includes a fragrance, a flavoring agent, a colorant and suspended particulate matter in the form of glitter in which the body gel is hypoallergenic and safe for the user.

Accordingly, it is an object of the present invention to provide a body gel having an ingredient composition that includes suspended particulate matter in the form of shaped glitter made from a colorized polyester glitter contained therein.

Another object of the present invention is to provide a body gel having an ingredient composition that also includes a fragrance, a flavoring agent, and a colorant.

Another object of the present invention is to provide a body gel that is made from cosmetic ingredients that are hypoallergenic and safe for the user to apply to the body (skin).

Another object of the present invention is to provide a body gel that imparts cosmetic and aesthetic qualities which enhance a female's appearance, beauty and sex appeal.

Another object of the present invention is to provide a body gel that is easy to apply and easy to remove and clean-off when the user deems it necessary to remove the shaped glitter from the user's body.

A further object of the present invention is to provide a body gel that is long lasting, durable in application and reliable in providing cosmetic conditioning.

A still further object of the present invention is to provide a body gel that may be mass produced in an automated and economical manner and being readily affordable by the consumer.

SUMMARY OF THE INVENTION

In the present invention, there is provided a body gel composition having glitter contained therein, including a surface active agent system for moisturizing the skin being in the range of 3 percent to 12 percent by weight of the body gel composition; at least one pH adjuster being in the range of 0.5% to 2.0% by weight of the body gel composition; a preservative system for preserving the body gel composition against microbial contamination being in the range of 0.40% to 2.4% by weight of the body gel composition; at least one anti-oxidant and light stabilizer for preventing oxidation of the body gel composition being in the range of 0.02% to 0.3% by weight of the body gel composition; a diluent in the form of water in the range of 50% to 70% by weight of the body gel composition; and suspended particulate matter having a plurality of predetermined glitter shapes for cosmetic ornamention of the body being in the range of 10.0% to 20.0% by weight of the body gel composition.

The body gel composition of the present invention may further include a fragrance component for imparting a characteristic scent to the body gel being in the overall range of 0.20% to 3.0% by weight of the body gel composition; a flavor component for imparting a characteristic taste to the body gel being in the overall range of 0.20% to 4.0% by weight of the body gel composition; and a colorant for imparting a characteristic color to the body gel being in the overall range of 0.10% to 2.0% by weight of the body gel composition.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 2 is a top plan view of the body gel having glitter with predetermined shapes of the present invention showing geometrically shaped glitter in the form of stars, sunbursts, hearts, crescents, tear drops, crosses, triangles, circles, squares and the like; and FIG. 3 is a top plan view of the body gel having glitter with predetermined shapes of the present invention showing non-geometrically shaped glitter in the form of animals, fish, fruit, insects, human characters and the like.

DETAILED DESCRIPTION OF THE PREFERRED EMBODIMENT

Figure 1:
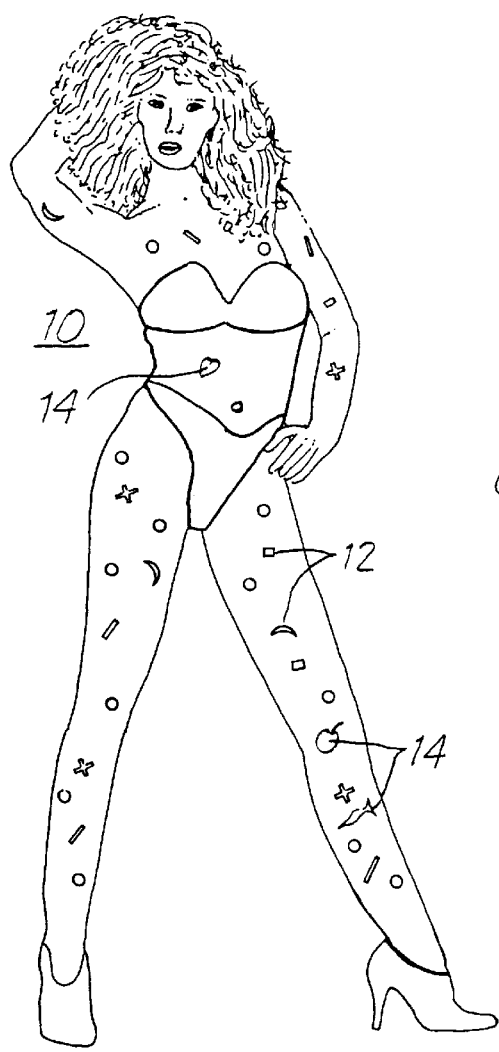
FIG. 1 is a front view of the body gel having glitter with predetermined shapes of the present invention showing the shaped glitter applied to the body.

In accordance with the body gel composition of the present invention, the ingredient categories of the constituent components include a surface active agent system, pH adjusters, a preservative system, an anti-oxidant and light stabilizer, water, a fragrance, a flavoring agent, a colorant, and suspended particulate matter having predetermined glitter shapes.

The surface active agent system of the body gel composition of the present invention is functionally defined to include chemical constituents that are chelates, gellants, humectants, moisturizers, thickeners, and or thixotropies. The surface active agent system of the body gel composition of the present invention is used for providing to the user the ability to retain moisture in the skin; to increase the moisture content of the skin through humectant barrier action; and to provide a thickened body gel which when applied to the skin areas of the body becomes more fluid. The surface active agent system for moisturizing the skin, as previously described above, includes chemical agents selected from the group consisting of propylene glycol, Carbomer 940™, bentonite, silk amino acids, decolorized aloe vera gel, honey extract, glycerin, collagen amino acids, triethanolamine, thixagel, hectorite, sepigel, trisodium EDTA, sodium aspartate, polysorbate, equivalent chemical agents and combinations thereof. The surface active agent system is at least 3% by weight of the body gel composition and has an overall range of 3% to 12% by weight of the body gel composition.

The pH adjusters for the body gel composition of the present invention are functionally defined to include chemical constituents that are acidulents, alkalinizers, buffers and/or neutralizers. The pH adjusters for the body gel composition of the present invention are used for neutralizing or buffering the body gel composition from an acidic or basic condition to a neutral pH of 7. The pH adjusters for neutralizing of the body gel are selected from the group consisting of sodium hydroxide, citric acid, triethanolamine, diethanolamine, glycine, ethanolamine, tromethamine, equivalents and combinations thereof, being in the overall range of 0.5% to 2.0% by weight of the body gel composition.

The preservative system for the body gel composition of the present invention is functionally defined to include chemical constituents that are antibacterial, antimicrobial and preservative agents for protecting the body gel composition from spoilage or contamination by microorganisms. The preservative system for protecting the user and the body gel composition against microbial contamination, as described above, are chemical agents selected from the group consisting of imidozolidinyl urea, methylparaben, propylparaben, benzylparaben, isopropylparaben, ethylparaben, Germaben II™, phenoxyisopropanol, Phenonip™, DMDM hydantoin, hexetidine, sorbic acid, honeysuckle extract, Iceland moss extract, equivalents and combinations thereof, being in the overall range of 0.40% to 2.4% by weight of the body gel composition.

The anti-oxidant and light stabilizer for the body gel composition of the present invention is defined to include chemical agents that are antioxidants and ultraviolet light absorbers. These chemical stabilizer agents are used to inhibit oxidation, rancidity, and protect the body gel composition from degradation by ultraviolet light radiation. These anti-oxidant and light stabilizers for protecting the body gel against oxidation and UV light damage, as described above, are chemical agents selected from the group consisting of benzophenone-2, octyl dimethyl PABA, octyl methoxycinnamate, BHA, octyl salicylate, ascorbic acid, isopropyl methoxycinnamate, equivalents and combinations thereof; being in the overall range of 0.02% to 0.3% by weight of the body gel composition.

Figure 2:
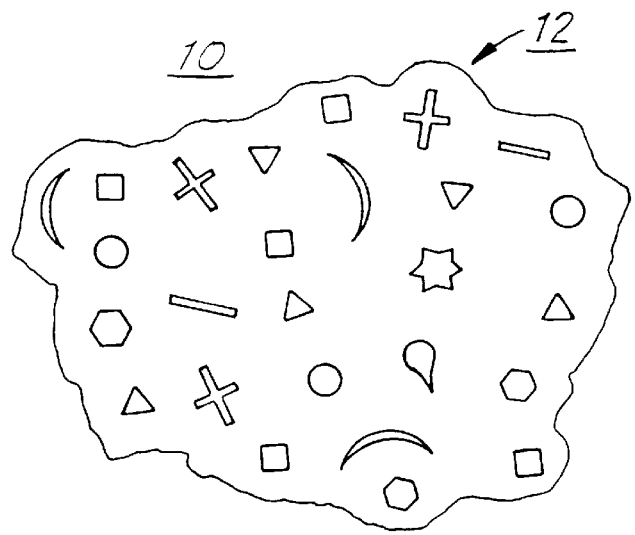
Figure 3:
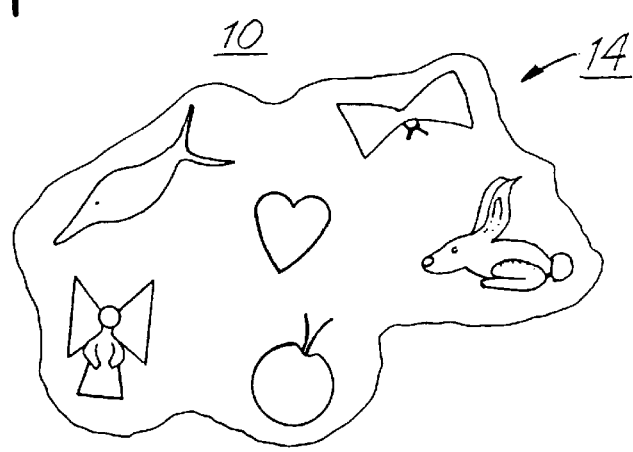

The suspended particulate matter 10, as shown in FIGS. 1 to 3, used for the body gel composition of the present invention is defined to include a pearlant chemical gannet that imparts a glitter, a sparkle or a pearlescent texture and luster to the cosmetic body gel product when exposed to natural or artificial light. These pearlant compounds are used for cosmetic ornamentation on selected parts of the user's body. The suspended particulate matter of the present invention is selected from the group consisting of colorized acrylic polyesters, metallic and non-metallic micas, bismuth oxychloride, organic guanines (fish scales), equivalents and combinations thereof, being in the overall range of 10.0% to 20.0% by weight of the body gel composition. In addition, the suspended particulate matter 10 may include glitter having various predetermined geometric shapes 12 or non-geometric shapes 14. Non-geometric shapes 14 may include silhouettes or holographic images of animals, fish, insects, flowers, human characters and the like. The predetermined geometric shaped glitter 12 may include silhouettes or holographic images that are selected from the group consisting of stars, sunbursts, snow flakes, tear drops, crescents, crosses, hearts, triangles, squares, rectangles, circles, ovals, octagons, pentagons, trapezoids and the like and equivalents thereof. The predetermined non-geometric shaped glitter 14 is selected from the group consisting of rabbits, cats, dogs, bears, deer, dolphins, sharks, minnows, butterflies, bees, roses, daises, tulips, babies, angels, and the like and equivalents thereof.

The fragrance (perfume) component of the body gel composition of the present invention is defined to impart a particular scent or characteristic aroma to the body gel composition. The use of a fragrance or perfume in the body gel composition provides an enhanced aesthetic quality to the body gel composition which heightens a female users' appearance, beauty and sex appeal. The fragrance component is selected from the group consisting of botanical extracts that include balm mint, birch, chamomile, fir, heather, honey suckle, ivy, jasmine, lotus, pine, rose, soapwort, violet, willow bark, winter green, witch hazel, yucca, and equivalents and combinations thereof, being in the overall range of 0.20% to 3.0% by weight of the body gel composition.

The flavor component for the body gel composition of the present invention is defined to impart a particular and characteristic taste and sometimes an aroma to the body gel composition. The use of a flavor component to the body gel composition also provides another enhanced aesthetic quality to the body gel which will intensify the female users' sex appeal. The flavor component is selected from the group consisting of water soluble botanical extracts that include apple, banana, cherry, cinnamon, cranberry, grape, honeydew, honey, kiwi, lemon, lime, orange, peach, peppermint, pineapple, raspberry, tangerine, watermelon, wild cherry, and equivalents and combinations thereof, being in the overall range of 0.20% to 4.0% by weight of the body gel composition.

The colorant component for the body gel composition of the present invention is defined to impart a characteristic color in conjunction with a particular flavor or fragrance to the body gel composition. For example, a yellow color is used for a banana flavor, or a pink color for a floral-type scent. The colorant component is selected from the group consisting of water soluble dyes that include FD&C dyes (food, drug, and cosmetic use dyes) of blue, green, orange, red, yellow and violet; iron oxide dyes; ultramarine pigments of blue, pink, red and violet; and equivalents thereof; being in the overall range of 0.10% to 2.0% by weight of the body gel composition. The dyes discussed above are well known, and are commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc.

The diluent or carrier is in the form of water in the overall range of 50.0% to 70.0% by weight of the body gel composition.

The following numbered examples illustrate representative body gel formulations embodying the present invention in using a scent or fragrance, a flavor, a colorant and suspended particulate matter within the body gel composition.

EXAMPLE 1

| PRODUCT DESCRIPTION: UNSCENTED GLITTER GEL | |
|---|---|
| CHEMICAL COMPONENT | PERCENTAGE BY WEIGHT |
| Water | 50.00–70.00 |
| Polyester glitter | 10.00–20.00 |
| Propylene glycol | 2.00–10.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Trisodium EDTA | 0.10–0.75 |
| Propylparaben | 0.02–0.40 |
| Benzophenone-2 | 0.02–0.30 |

EXAMPLE 2

| PRODUCT DESCRIPTION: SCENTED GLITTER GEL | |
|---|---|
| CHEMICAL COMPONENT | PERCENTAGE BY WEIGHT |
| Water | 50.00–70.00 |
| Polyester glitter | 10.00–20.00 |
| Propylene glycol | 2.00–10.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Trisodium EDTA | 0.10–0.75 |
| Propylparaben | 0.02–0.40 |
| Benzophenone-2 | 0.02–0.30 |
| Rose fragrance | 0.20–3.0 |

EXAMPLE 3

| PRODUCT DESCRIPTION: SCENTED AND COLORED GLITTER GEL | |
|---|---|
| CHEMICAL COMPONENT | PERCENTAGE BY WEIGHT |
| Water | 50.00%–70.00% |
| Polyester glitter | 10.00–20.00 |
| Propylene glycol | 2.00–10.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Trisodium EDTA | 0.10–0.75 |
| Propylparaben | 0.02–0.40 |
| Benzophenone-2 | 0.02–0.30 |
| Rose fragrance | 0.20–3.00 |
| Ultramarine pink pigment | 0.10–2.00 |

EXAMPLE 4

| PRODUCT DESCRIPTION: FLAVORED GLITTER GEL | |
|---|---|
| CHEMICAL COMPONENT | PERCENTAGE BY WEIGHT |
| Water | 50.00%–70.00% |
| Polyester glitter | 10.00–20.00 |
| Propylene glycol | 2.00–10.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Trisodium EDTA | 0.10–0.75 |
| Propylparaben | 0.02–0.40 |
| Benzophenone-2 | 0.02–0.30 |
| Cinnamon flavor | 0.20–4.0% |

EXAMPLE 5

| PRODUCT DESCRIPTION: COLORED AND FLAVORED GLITTER GEL | |
|---|---|
| CHEMICAL COMPONENT | PERCENTAGE (%) BY WEIGHT |
| Water | 50.00–70.00 |
| Polyester glitter | 10.00–20.00 |
| Propylene glycol | 2.00–10.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Trisodium EDTA | 0.10–0.75 |
| Propylparaben | 0.02–0.40 |
| Benzophenone-2 | 0.02–0.30 |
| FD&C yellow dye | 0.10–2.00 |
| Banana flavor | 0.20–4.00 |

EXAMPLE 6

| PRODUCT DESCRIPTION: ORGANIC GLITTER GEL | |
|---|---|
| CHEMICAL COMPONENT | PERCENTAGE (%) BY WEIGHT |
| Water | 50.00–70.00 |
| Guanine | 10.00–20.00 |
| Aloe vera gel | 2.00–10.00 |
| Thixagel | 0.50–2.00 |
| Citric acid triethanolamine | 0.50–2.00 |
| Imidozolidinyl urea | 0.20–1.00 |
| DMDD hydantoin | 0.20–1.00 |
| Polysorbate | 0.10–0.75 |
| Honeysuckle extract | 0.02–0.40 |
| Ascorbic acid | 0.02–0.30 |
| FD&C yellow dye | 0.10–2.00 |
| Banana flavor | 0.20–4.00 |

ADVANTAGES OF THE PRESENT INVENTION

Accordingly, an advantage of the present invention is that it provides for a body gel having an ingredient composition that includes suspended particulate matter in the form of shaped glitter made from a colorized polyester glitter contained therein.

Another advantage of the present invention is that it provides for a body gel having an ingredient composition that also includes a fragrance, a flavoring agent, and a colorant.

Another advantage of the present invention is that it provides for a body gel that is made from cosmetic ingredients that are hypoallergenic and safe for the user to apply to the body (skin).

Another advantage of the present invention is that it provides for a body gel that imparts cosmetic and aesthetic qualities which enhance a female's appearance, beauty and sex appeal.

Another advantage of the present invention is that it provides for a body gel that is easy to apply and easy to remove and clean-off when the user deems it necessary to remove the shaped glitter from the user's body.

A further advantage of the present invention is that it provides for a body gel that is long lasting, durable in application and reliable in providing cosmetic conditioning.

A still further advantage of the present invention is that it provides for a body gel that may be mass produced in an automated and economical manner and being readily affordable by the consumer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A body gel composition having glitter contained therein, comprising:
    a) a surface active agent system for moisturizing the skin selected from the group consisting of bentonite, silk amino acids, honey extract, collagen amino acids, thixagel, hectorite, sepigel, trisodium EDTA, and sodium aspartate; being in the range of 3.0% to 12.0% by weight of the body gel composition;
    b) at least one pH adjuster selected from the group consisting of diethanolamine, glycine, ethanolamine, tromethamine, and combinations thereof; being in the range of 0.5% to 2.0% by weight of the body gel composition;
    c) a preservative system for preserving the body gel composition against microbial contamination selected from the group consisting of benzylparaben, isopropylparaben, ethylparaben, Germaben II™, phenoxyisopropanol, Phenonip™, DMDM hydantoin, hexetidine, sorbic acid, honeysuckle extract, Iceland moss extract and combinations thereof; being in the range of 0.40% to 2.4% by weight of the body gel composition;
    d) at least one anti-oxidant and light stabilizer for preventing oxidation of the body gel composition selected from the group consisting of benzophenone-2, octyl dimethyl PABA, octyl methoxycinnamate, BHA, octyl salicylate, ascorbic acid, isopropyl methoxycinnamate, and combinations thereof, being in the range of 0.02% to 0.3% by weight of the body gel composition;
    e) a diluent in the form of water in the range of 50.0% to 70.0% of the body gel composition; and
    f) suspended particulate matter for cosmetic ornamentation of the body selected from the group consisting of colorized acrylic polyester, metallic and non-metallic micasbismuth oxychloride, and organic guanines being in the range of 10.0% to 20.0% by weight of the body gel composition, said suspended particulate matter having a plurality of different predetermines shapes.

2. A body gel composition in accordance with claim 1, wherein said surface active agent system is at least 3.0% by weight of the body gel composition.

3. A body gel composition in accordance with claim 1, further including a fragrance component for imparting a characteristic scent to said body gel composition selected from the group consisting of botanical extracts that include balm mint, birch, chamomile, fir, heather, honey suckle, ivy, jasmine, lotus, pine, rose, soapwort, violet willow bark, Winter green, witch hazel, and yucca; being in the overall range of 0.20% to 3.0% by weight of the body gel composition.

4. A body gel composition in accordance with claim 1, further including a flavor component for imparting a characteristic taste to said body gel composition selected from the group consisting of water soluble botanical extracts that include apple, banana, cherry, cinnamon, cranberry, grape, honeydew, honey, kiwi, lemon, lime, orange, peach, peppermint, pineapple, raspberry, tangerine, watermelon, and wild cherry; being in the overall range of 0.20% to 4.0% by weight of the body gel composition.

5. A body gel composition in accordance with claim 1, further including a colorant component for imparting a characteristic color to said body gel composition selected from the group consisting of water soluble dyes of blue, green, orange, red, violet, and yellow; iron oxide dyes; ultramarine pigments of blue, pink, red, and violet; being in the overall range of 0.10% to 2.0% by weight of the body gel composition.

6. A body gel composition in accordance with claim 1, wherein said suspended particulate matter includes objects having predetermined geometric shapes.

7. A body gel composition in accordance with claim 6, wherein said predetermined geometric shapes are selected from the group consisting of objects having the shapes of stars, sunbursts, snow flakes, tear drops, crescents, crosses, hearts, triangles, squares, rectangles, circles, ovals, octagons, pentagons, and trapezoids.

8. A body gel composition in accordance with claim 1, wherein said suspended particulate matter includes objects having predetermined non-geometric shapes selected from the group consisting of objects in the shape of animals, fish, insects, flowers, fruits, and human characters.

9. A body gel composition in accordance with claim 8, wherein said predetermined non-geometric shapes are selected from the group consisting of objects having the shapes of rabbits, cats, dogs, bears, deer, dolphins, sharks, minnows, butterflies, bees, roses, daises, tulips, babies, and angels.

10. A body gel composition in accordance with claim 1, wherein said suspended particulate matter having a plurality of different predetermined shapes are holographic objects.

* * * * *